United States Patent
Wang et al.

(10) Patent No.: US 10,377,865 B2
(45) Date of Patent: Aug. 13, 2019

(54) 3D PRINTABLE BIODEGRADABLE POLYMER COMPOSITE

(71) Applicant: National Tsing Hua University, Hsinchu (TW)

(72) Inventors: Jane Wang, Hsinchu (TW); Yih-Lin Cheng, Taipei (TW); Yi-Wen Chen, Taichung (TW); Ming-You Shie, Kaohsiung (TW)

(73) Assignee: National Tsing Hua University, Hsinchu (TW)

( * ) Notice: Subject to any disclaimer, the term of this patent is extended or adjusted under 35 U.S.C. 154(b) by 0 days.

(21) Appl. No.: 15/859,802

(22) Filed: Jan. 2, 2018

(65) Prior Publication Data

US 2019/0048151 A1     Feb. 14, 2019

(30) Foreign Application Priority Data

Aug. 10, 2017  (TW) .............................. 106126999 A (51) Int. Cl.

| | |
|---|---|
| *C08F 2/46* | (2006.01) |
| *C08F 2/50* | (2006.01) |
| *C08G 61/04* | (2006.01) |
| *C08J 3/28* | (2006.01) |
| *A61L 27/16* | (2006.01) |
| *A61L 33/06* | (2006.01) |
| *A61L 31/14* | (2006.01) |
| *C08F 299/04* | (2006.01) |
| *C08F 299/02* | (2006.01) |
| *B33Y 70/00* | (2015.01) |
| *A61L 27/58* | (2006.01) |

(52) U.S. Cl.
CPC ................. *C08J 3/28* (2013.01); *A61L 27/16* (2013.01); *A61L 27/58* (2013.01); *A61L 31/148* (2013.01); *A61L 33/064* (2013.01); *B33Y 70/00* (2014.12); *C08F 299/028* (2013.01); *C08F 299/0492* (2013.01); *C08J 2353/00* (2013.01)

(58) Field of Classification Search
USPC ........... 522/48, 47, 6, 71, 189, 184, 1; 520/1
See application file for complete search history.

(56) References Cited

U.S. PATENT DOCUMENTS

| | | | |
|---|---|---|---|
| 2009/0274877 A1* | 11/2009 | Chan ....................... | B32B 33/00 428/167 |
| 2013/0123384 A1* | 5/2013 | Grijpma .............. | C08F 299/024 522/163 |

OTHER PUBLICATIONS

Nijst et al, Synthesis and characterization of Photocurable Elastomers from poly(glycerol-c-sebacate), Oct. 2007, Biomacromolecules, 8(10), 3067-3073 (Year: 2007).*
Loh et al, Poly(glycerol sebacate) biomaterial: synthesis and biomedical applications, 2015, J. Mater. Chem. B., 3, 7641-7652 (Year: 2015).*

* cited by examiner

*Primary Examiner* — Jessica Whiteley
(74) *Attorney, Agent, or Firm* — Alan D. Kamrath; Mayer & Williams PC (57) ABSTRACT

A printable biodegradable polymer composite includes PGSA, a biodegradable photo-initiator and material selected from the group consisting PCL-DA and PEG-DA uniformly blended together. By adjusting the blending ratio, the elasticity, mechanical properties and degradation patterns may be adjusted for producing a tissue, organ or related bioproduct by 3D-printing.

2 Claims, 10 Drawing Sheets

3D PRINTABLE BIODEGRADABLE POLYMER COMPOSITE

BACKGROUND OF THE INVENTION

1. Field of the Invention

The present invention relates to a polymer composite and, more particularly, to a 3D printable biodegradable polymer composite.

2. Description of Related Art

Biomaterial has been widely used in the medical device and bio-engineering field. By interacting with the human body system, biocompatible biomaterial is able to repair or even replace damaged or nonfunctional tissues and organs. Since biomaterial is directly applied to the human body, physical and chemical properties of the biomaterial are critical. Biocompatibility and biodegradability of the biomaterial are important factors that need to be concerned.

Biomaterial can be divided into several different types of applications. According to its requirements of mechanical, hardness and elasticity properties, most common divisions of biomaterial contain polymers, ceramic, metal and composites. Ceramic and metal materials are normally used as replacements for human hard tissue like bones. Polymers and composites are mainly used as replacements for human soft tissue like organs.

Uncontrollable mechanical property and unpredictable bio-degradability are some limitations and shortcomings that need to be concerned for the conventional biomaterial. To overcome the shortcomings, the present invention provides a printable biodegradable polymer composite to mitigate or obviate the aforementioned problems.

SUMMARY OF THE INVENTION

The main objective of the present invention is to provide a 3D printable biodegradable polymer composite comprising: poly(glycerol sebacate acrylate), a photo-initiator and a material selected from the group consisting of polycaprolactone-diacrylate and polyethyleneglycol-diacrylate uniformly blended together, with a degree of an acrylation of poly(glycerol sebacate acrylate) being at a range of 5%~60%.

According to abovementioned properties, the present invention has advantages as follows.

1. By adjusting a blending ratio of PGSA, PCL-DA and PEG-DA, the present invention is able to produce products with different elasticity, mechanical, degradability and elongation properties by 3D printing. The present invention is suitable for producing human tissue or organs in bio-engineering.

2. The present invention is able to be cured under UV or visible light which is suitable for rapid tooling like 3D printing and is suitable for producing customized products corresponding to human tissue, organs or other related applications With adjustable elasticity, mechanical, degradability and elongation properties, the present invention is able to solve the problems of the conventional bio-material.

Other objectives, advantages and novel features of the invention will become more apparent from the following detailed description when taken in conjunction with the accompanying drawings.

DETAILED DESCRIPTION OF THE PREFERRED EMBODIMENTS

The present invention is related to a three-dimensional (3D) printable biodegradable polymer composite comprising PGSA(Poly(glycerol sebacate acrylate)), a photo-initiator 0.05~5 wt % and a material selected from the group consisting of PCL-DA (Polycaprolactone-diacrylate) and PEG-DA(Polyethyleneglycol-diacrylate) uniformly blended together. The degree of acrylation of PGSA in the present invention is preferred at a range of 5%~60% and more preferred at the range of 7%~30%. A blending ratio of the combination of PGSA and PCL-DA in the present invention is preferred at a range of PGSA 60~90 wt % and PCL-DA 10~40%. A blending ratio of the combination of PGSA and PEG-DA in the present invention is preferred at a range of PGSA 30~70 wt % and PEG-DA 30~70%. A blending ratio of the combination of PGSA, PCLG-DA and PEG-DA in the present invention is preferred at a range of PGSA 30~50 wt %, PCL-DA 30~40% and PEG-DA 20~30 wt %.

PGSA, PCL-DA and PEG-DA of the present invention are bio-compatible and bio-degradable material. By grafting PCL and PEG with the diacrylate (DA) functional group, PCL-DA and PEG-DA are able to form a strong crosslink reaction with PGSA after curing under a certain light wave.

The photo-initiator of the present invention is preferred to be a bio-compatible material. The photo-initiator of the present invention may be, but is not limited to, TPO(diphenyl(2,4,6-trimethylbenzoyl)phosphine oxide), Irgacure 784™ prefluorinated dipheny titanocene or Camphorquinone (CQ). TPO and Irgacure 784™ prefluorinated dipheny titanocene can be activated under UV light or visible light. Camphorquinone can be activated under visible light.

PGSA of the present invention is preferably produced by grafting PGS(Poly(glycerol sebacate)) with a solution containing a different ratio of acryloyl chloride, triethylamine, 4-dimethylamino pyridine (DMAP) and dichloromethane (DCM). With reference to the below chart 1, some preferred embodiments of the present invention are shown for producing PGSA with 7~30% degree of acrylation.

CHART 1

| Group | Material | | | | | |
| --- | --- | --- | --- | --- | --- | --- |
|  | PGS (g) | Acryloyl chloride (ml) | Triethylamine (ml) | DMAP (mg) | DCM (ml) | PGSA (%) |
| Group 1 | 30 | 1.42 | 3.06 | 30 | 300 | 7 |
| Group 2 | 30 | 2.84 | 6.13 | 30 | 300 | 15 |
| Group 3 | 30 | 5.69 | 12.26 | 30 | 300 | 30 |

Besides the abovementioned triethylamine, potassium carbonate (K2CO3) may also be used for producing PGSA with a different degree of acrylation. By utilizing potassium carbonate ($K_2CO_3$), a less toxic or non-biocompatible solvent will be used during the production which may lead to better bio-compatibility for PGSA.

In order to obtain the 3D printable biodegradable polymer composite of the present invention, it is preferred to blend the PGSA, the photo-initiator, PCL-DA and PEG-DA in dichloromethane. After abstracting the dichloromethane, the 3D printable biodegradable polymer composite of the present invention is produced.

In order to prove the mechanical property and bio-degradability of the present invention are adjustable, testing blocks are produced by 3D printing with a different acrylation degree of PGSA or a different blending ratio of the main materials of the present invention (PGSA, the photo-initiator, PCL-DA and PEG-DA). Each testing block is produced by depositing 5 layers of blended materials and 100 μm thicknesses in each layer. During depositing, the first layer of the testing block is cured by exposing to a UV/visible light in 30 seconds. The second to fifth layers of the testing blocks are cured by exposing to a UV/visible light in 15 seconds.

The first embodiment of the present invention are 3D printed testing blocks comprising PGSA, PCL-DA and the photo-initiator with the PGSA and PCL-DA having a blending ratio of 2:1 and with the photo-initiator at a range of 1~5 wt %. The PGSA of the first embodiment has 7%~30% of acrylation. Test results show that Young's Modules of the testing blocks in the first embodiment are increased from 1.42 MPa to 6.4 MPa as the acrylation of PGSA increased. Ultimate tensile strength (UTS) of the testing blocks in the first embodiment increases from 0.19 MPa to 0.69 MPa as the acrylation of PGSA increased.

The second embodiment of the present invention are 3D printed testing blocks comprising PGSA, PCL-DA and the photo-initiator, with the PGSA and PCL-DA having a blending ratio of 2:1~4:1 and with the photo-initiator at a range of 1~5 wt %. The PGSA of the second embodiment has 15% of acrylation. Test results show that Young's Modules of the testing blocks in the second embodiment are slightly decreased from 2.85 MPa to 2.3 MPa as the blending ratio of PGSA increased. Elongation at a break of the testing blocks in the second embodiment otherwise increased from 11.28% to 19.27% as the blending ratio of PGSA increased. After 24 days, the degradation rate of the testing blocks in the second embodiment also increased from 11.28% to 19.27% as the blending ratio of PGSA increased. Hence, elasticity and degradability of the present invention may be adjusted with a different blending ratio of PGSA and PCL-DA.

The third embodiment of the present invention are 3D printed testing blocks comprising PGSA, PEG-DA and the photo-initiator, with the PGSA and PEG-DA having a blending ratio of 1:1 and with the photo-initiator at a range of 1~5 wt %. The PGSA of the third embodiment has 7%~30% of arcylation. Test results show that Young's Modules of the testing blocks in the third embodiment increased from 4.25 MPa to 10.54 MPa as the acrylation of PGSA increased. Ultimate tensile strength (UTS) of the testing blocks in the third embodiment increased from 0.8 MPa to 1.1 MPa as the acrylation of PGSA increased. According to the aforementioned test result, the mechanical property of the present invention may be adjusted according to PGSA with a different degree of acrylation.

The fourth embodiment of the present invention are 3D printed testing blocks comprising PGSA, PEG-DA and the photo-initiator, with the PGSA and PEG-DA having a blending ratio of 1:1~2:1 and with the photo-initiator at a range of 1~5 wt %. The PGSA of the fourth embodiment has 15% of arcylation. Test results show that Young's Modules of the testing blocks in the fourth embodiment slightly decreased from 7.58 MPa to 4.66 MPa as the blending ratio of PGSA increased. Elongation at a break of the testing blocks in the fourth embodiment otherwise increased from 13.63% to 18.41% as the blending ratio of PGSA increased. After 24 days, the degradation rate of the testing blocks in the fourth embodiment also increased from 13.63% to 18.41% as the blending ratio of PGSA increased. Hence, elasticity and degradability of the present invention may be adjusted with a different blending ratio of PGSA and PEG-DA.

The fifth embodiment of the present invention are 3D printed testing blocks comprising PGSA, PCL-DA, PEG-DA and the photo-initiator, with the PGSA, PCL-DA and PEG-DA having a blending ratio of 1:1:1~2:1:1 and with the photo-initiator at a range of 1~5 wt %. The PGSA of the fifth embodiment has 30% of arcylation. Test results show that ultimate tensile strength (UTS) of the testing blocks in the fifth embodiment increased from 0.40 MPa to 0.93 MPa as the blending ratio of PGSA increased. After 24 days, the degradation rate of the testing blocks in the fifth embodiment also increased from 10.55% to 25.05% as the blending ratio of PGSA increased. Young's Modules of the testing blocks in the fifth embodiment slightly decreased from 4.32 MPa to 3.58 MPa as the blending ratio of PGSA increased.

The sixth embodiment of the present invention are 3D printed testing blocks comprising PGSA, PCL-DA, PEG-DA and the photo-initiator, with the PGSA, PCL-DA and PEG-DA having a blending ratio of 1:1:1~1:1:2 and with the photo-initiator at a range of 1~5 wt %. The PGSA of the sixth embodiment has 30% of arcylation. Test results show that Young's Modules of the testing blocks in the fifth embodiment slightly decreased from 4.32 MPa to 6.38 MPa as the blending ratio of PCL-DA increased. Ultimate tensile strength (UTS) of the testing blocks in the sixth embodiment increased from 0.40 MPa to 1.28 MPa as the blending ratio of PCL-DA increased.

According to abovementioned embodiments, the present invention is able to produce 3D printing products with a different mechanical property and a different degradability by adjusting the blending ratio of PGSA, PCL-DA and PEG-DA and adjusting the acrylation degrees of PGSA.

In order to prove the present invention is suitable for 3D printing, the control groups are provided by directly coating the aforementioned materials in each embodiment on films and cured under UV light. Test results show that Young's Modulus of the control groups increase from 0.57 MPa to only 4.08.

Comparing to coating, the reason why the present invention has a better mechanical property when produced by 3D printing is that materials are able to be quickly shaped and cured without any precipitate being formed while 3D printing. This may enhance uniformity and mechanical property of materials which leads to better mechanical property of the present invention.

With reference to FIG. 1 to FIG. 4, Young's Modulus, ultimate tensile strength, elongation at break and degradation rate of other embodiments in the present invention are presented. Samples with blending ratios of 1:0, 4:1 and 2:1 represent PGSA0%, 80% and 33% blended with PCL-DA. The acrylation degrees of PGSA in these samples are 7%, 15% and 30%.

With reference to FIG. 1 to FIG. 4, the sample with a blending ratio 4:1 shows lesser mechanical property than the sample with a blending ratio of 1:0. The mechanical property can be reduced by the existence of PGSA which is suitable for applying to soft tissue. Samples with blending ratios 4:1 and 2:1 show hardness of material increased as the acrylation degree of PGSA decreased. As the blending ratio of PCL-DA increased, the mechanical property of samples otherwise increased with elasticity remaining. As the acrylation degree of the PGSA increased, mechanical properties of these samples are only slightly effected as the blending ratio of PCL-DA increased.

Figure 1:
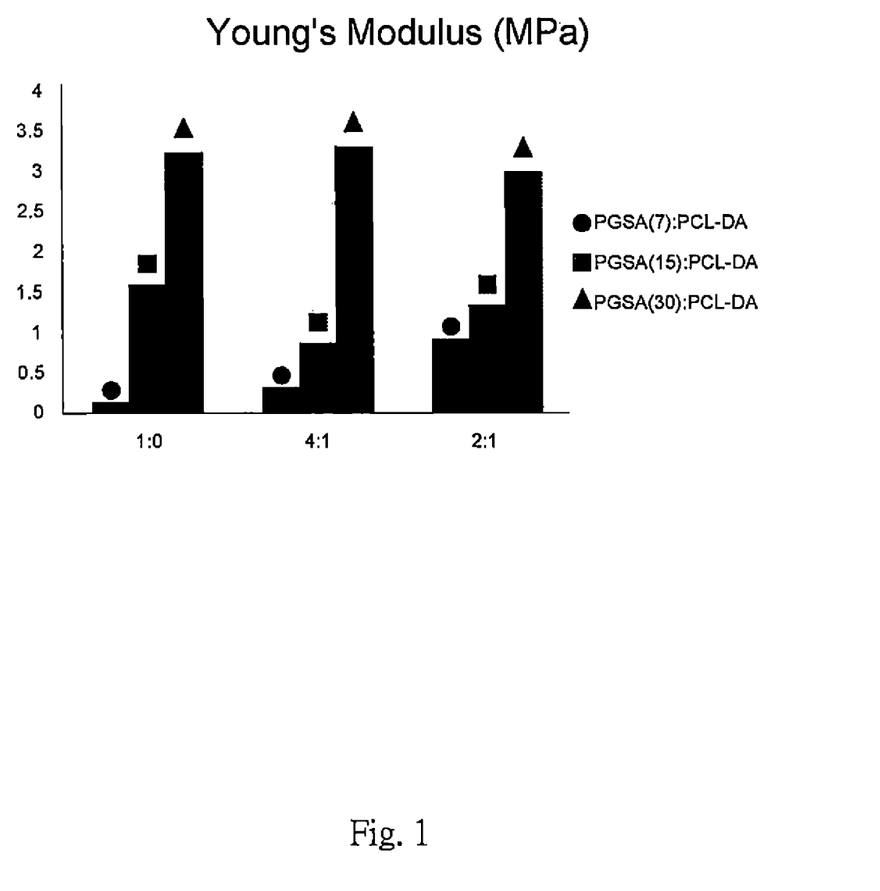
FIG. 1 is Young's Modulus of a preferred embodiment in accordance with the present invention.
Figure 2:
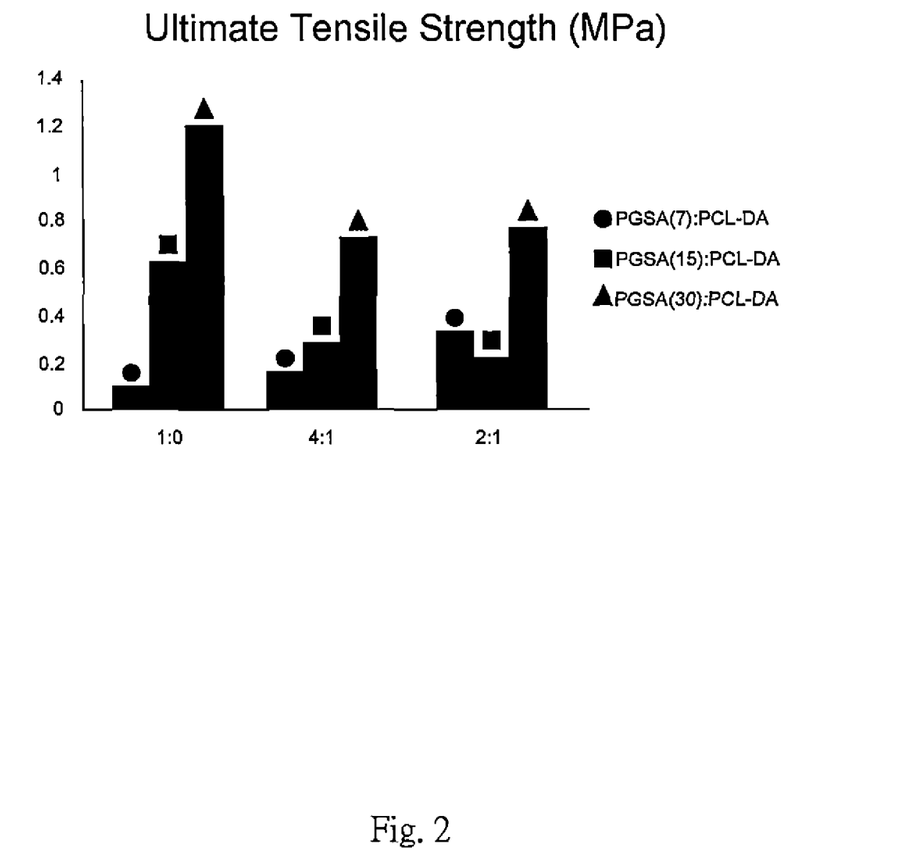
FIG. 2 is an ultimate tensile strength of the preferred embodiments in accordance with the present invention.
Figure 3:
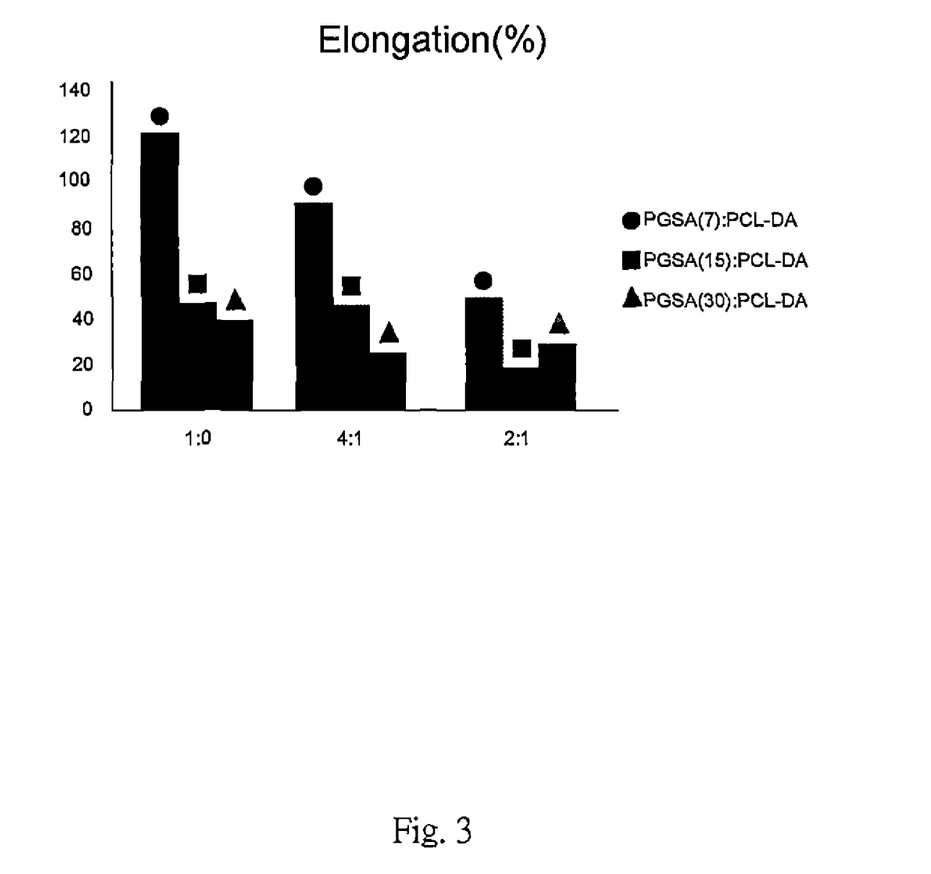
FIG. 3 is elongation at a break of the preferred embodiments in accordance with the present invention.
Figure 4:
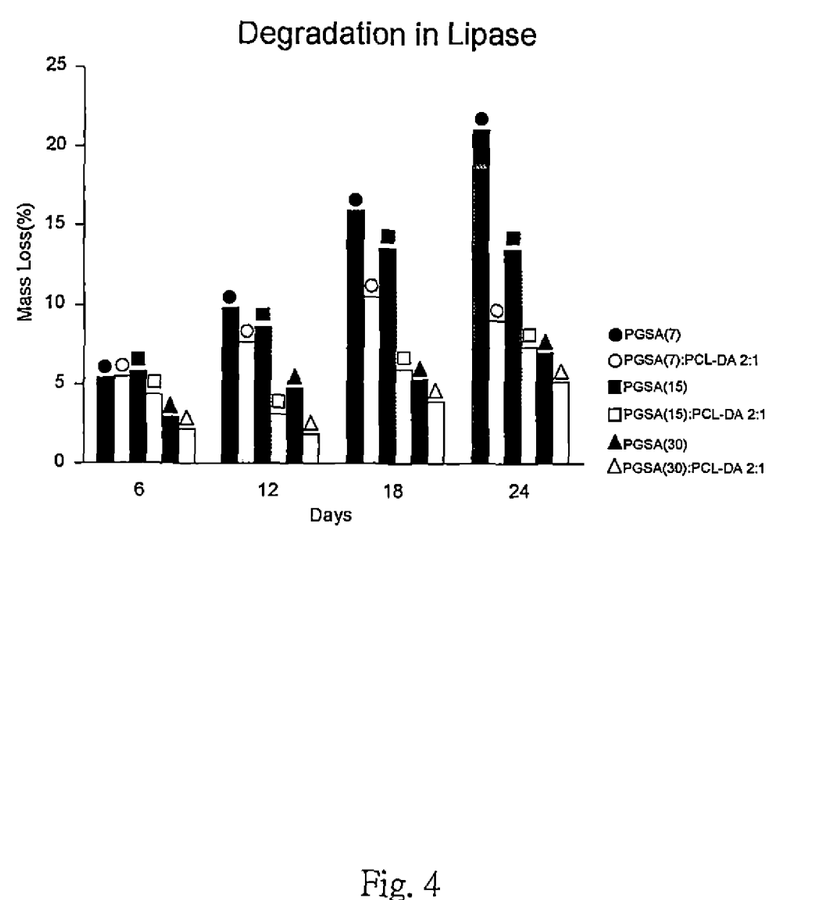
FIG. 4 is a degradation rate of the preferred embodiments in accordance with the present invention.
Figure 5:
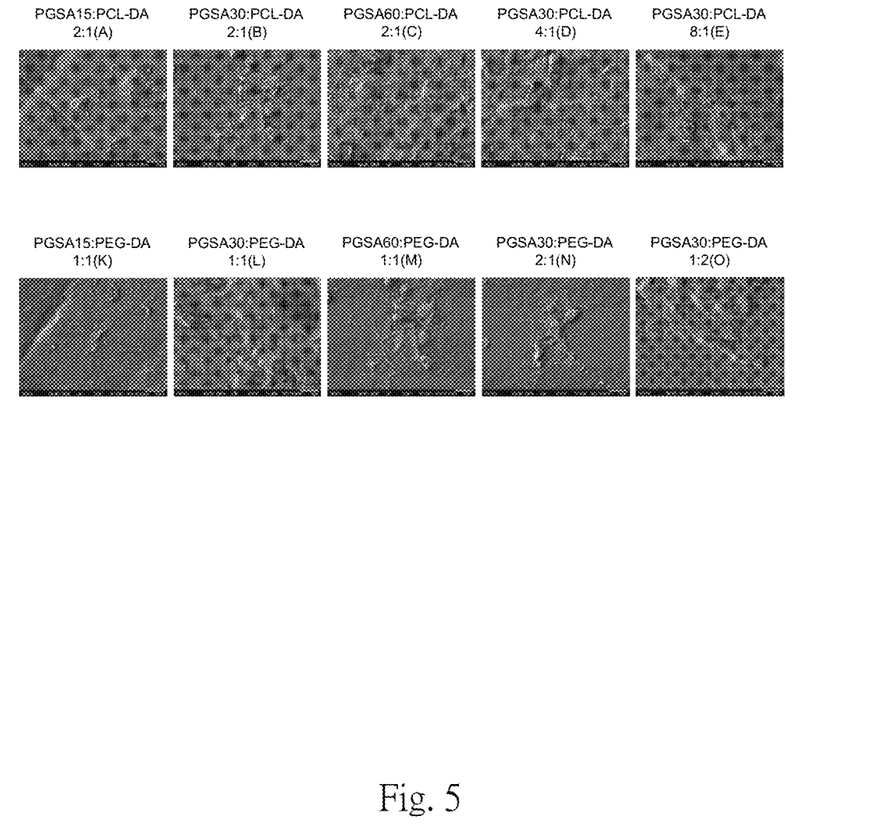
FIG. 5 is a SEM of stem cells for showing bio-compatibility in accordance with the present invention.
Figure 6:
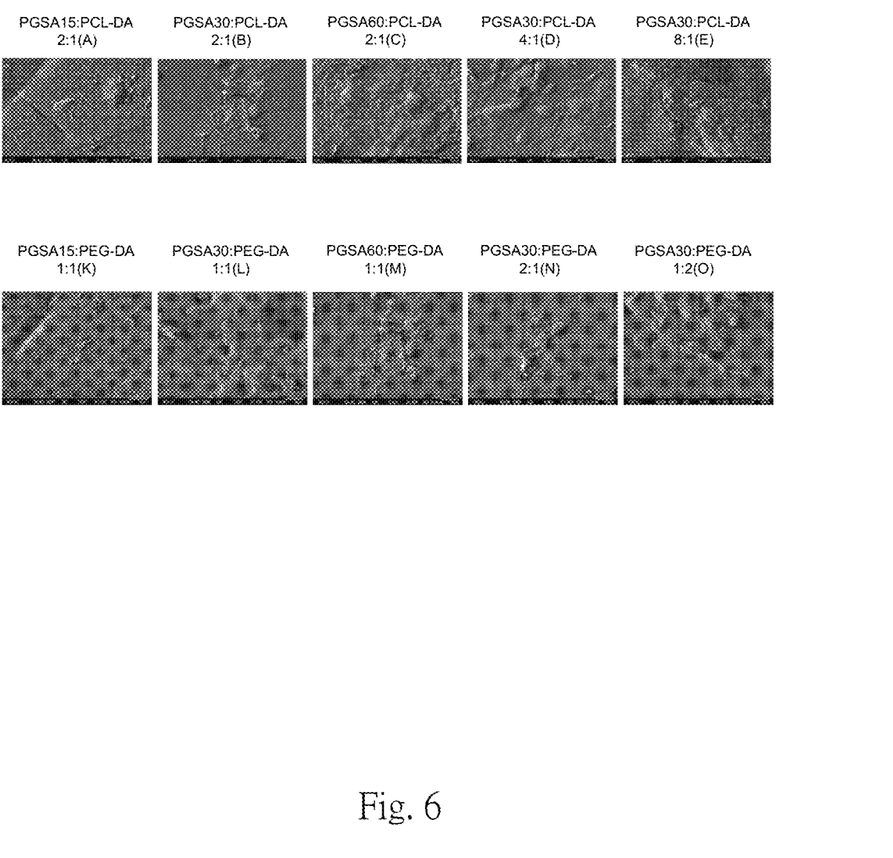
FIG. 6 is a SEM of human pulmonary alveolar epithelial cells showing bio-compatibility in accordance with the present invention.

With reference to FIG. 5 to FIG. 6, SEM pictures for showing bio-compatibility of stem cells and human pulmonary alveolar epithelial cells are presented by utilizing the embodiments of the present invention as mentioned above. Samples A to O shown in FIG. 5 and FIG. 6 are presented with a great bio-compatibility of the present invention.

Figure 7:
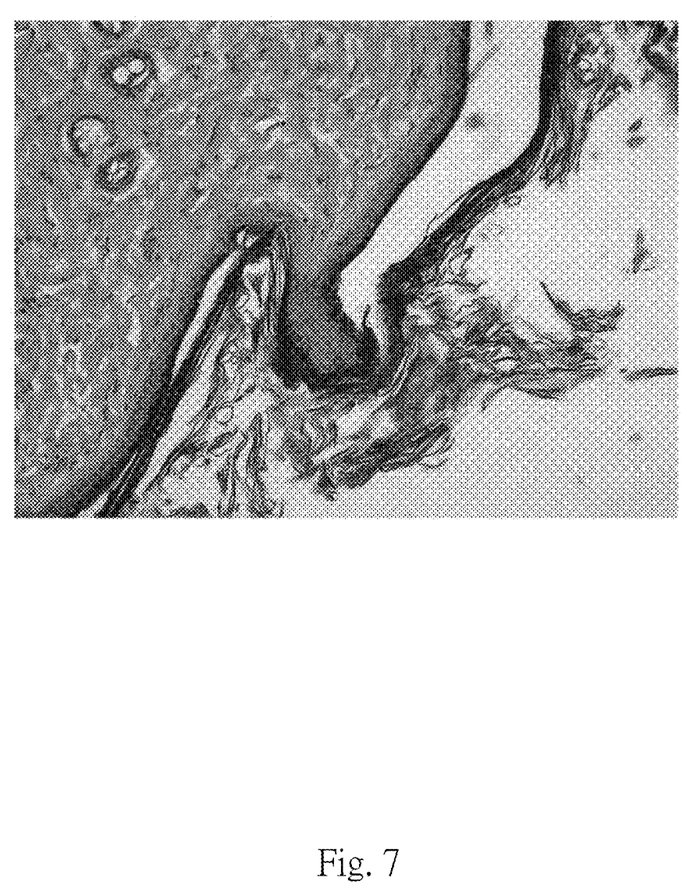
FIG. 7 is a hematoxylin and eosin-stained picture showing degradability of sample A in accordance with the present invention.
Figure 8:
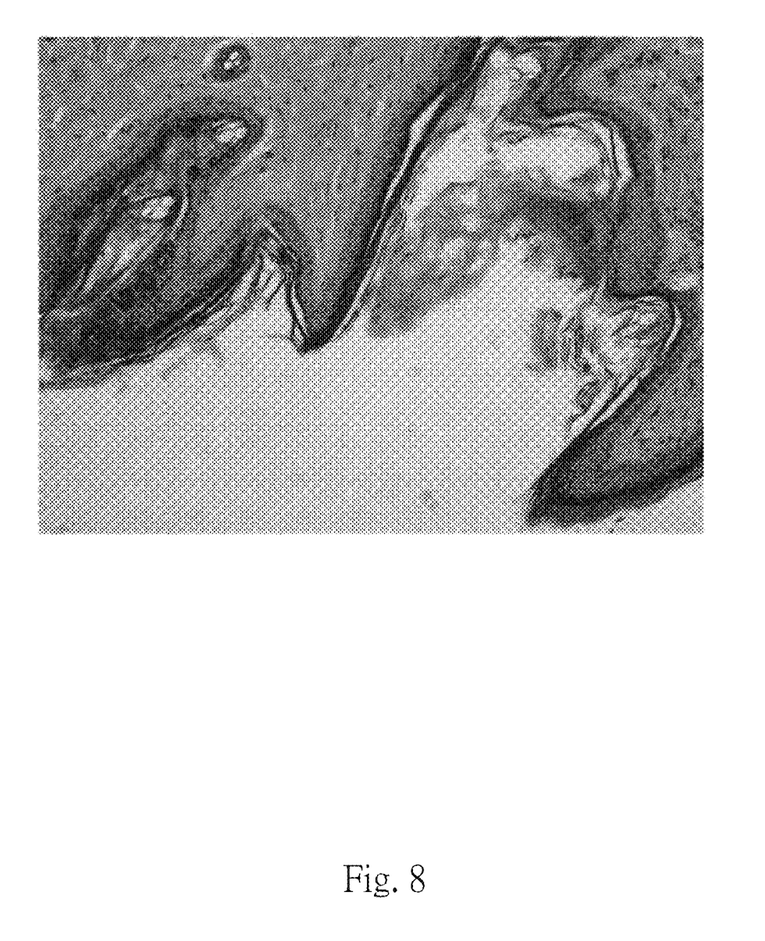
FIG. 8 is a hematoxylin and eosin-stained picture showing degradability of sample C in accordance with the present invention.
Figure 9:
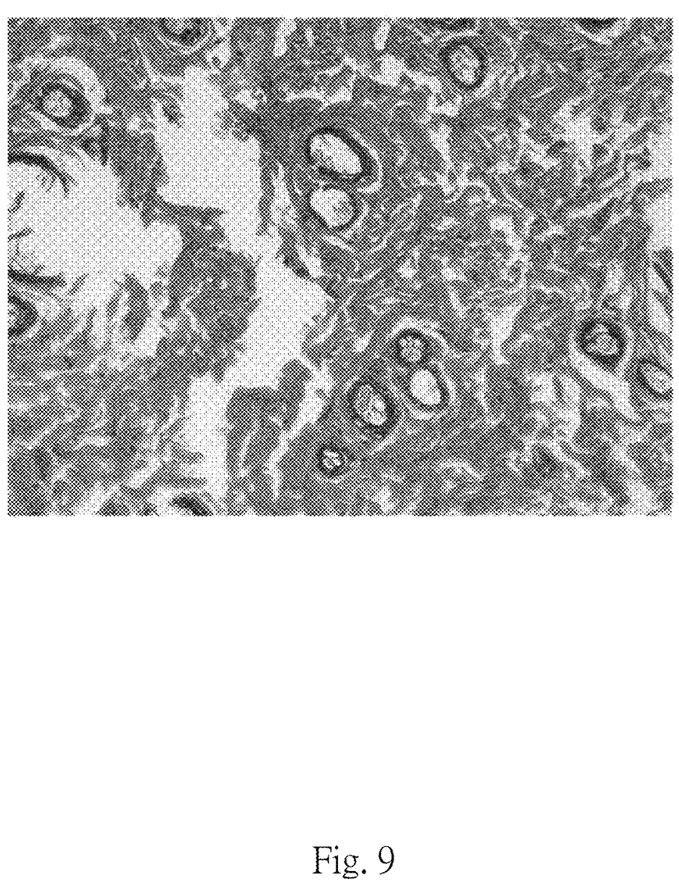
FIG. 9 is a hematoxylin and eosin-stained picture showing degradability of sample H in accordance with the present invention.
Figure 10:
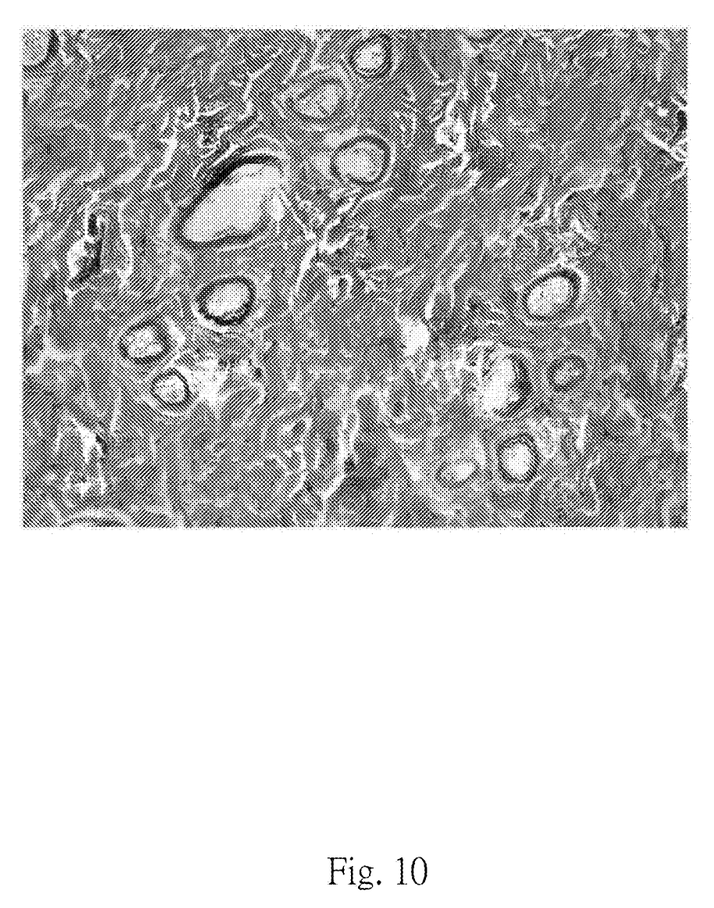
FIG. 10 is a hematoxylin and eosin-stained picture showing degradability of sample J in accordance with the present invention.

With reference to FIG. 7 to FIG. 10, Hematoxylin and eosin-stained (H&E stain) pictures for showing degradability of the present invention are presented. Samples shown in FIG. 7 and FIG. 8 comprise PGSA and PCL-DA corresponding to the samples A and C in FIG. 5 and FIG. 6. Samples shown in FIG. 9 and FIG. 10 comprise PGSA and PEG-DA corresponding to the samples H and J in FIG. 5 and FIG. 6. Degradability of samples in FIG. 7 and FIG. 8 are layered degradation which is gradually degraded layer by layer from outside to inside of the structure. Layered degradation is able to continually maintain mechanical property while degradation, which is suitable for applying to applications with high mechanical property demands. Degradability of samples shown in FIG. 9 and FIG. 10 are bulk degradation which is broke down in bulks by bulks. Since the degradation surface increases, bulk degradation is able to be quickly degraded which is suitable for applying to applications requiring a high degradation rate.

Post treatment may be applied to further increase the mechanical property of the present invention. The post treatment may be, but is not limited to, exposure to light or heat.

With reference to below chart 2, some bio-engineering applications are demonstrated according to the mechanical property, degradability and bio-compatibility of the main materials of the present invention. The present invention may be utilized to produce various human organ/tissue substitutes. Chart 2 is just some application examples of the present invention when applying to the bio-engineering field. The present invention is not limited to the examples shown in chart 2.

CHART 2

|  | Suitable for producing human organ/tissue |
|---|---|
| PGSA + PCL-DA | Heart, liver |
| PGSA + PEG-DA | Heart |
| PGSA + PCL-DA + PEG-DA | Cartilage |

According to the abovementioned properties, the present invention has advantages as follows.

1. By adjusting the blending ratio of PGSA, PCL-DA and PEG-DA, the present invention is able to produce products with different elasticity, mechanical, degradability and elongation properties by 3D printing. The present invention is suitable for producing human tissue or organs in bio-engineering.

2. The present invention is able to be cured under UV or visible light which is suitable for rapid tooling like 3D printing and is suitable for producing customized products corresponding to human tissue, organs or other related applications 3. With adjustable elasticity, mechanical, degradability and elongation properties, the present invention is able to solve the problems of the conventional bio-material.

What is claimed is:

1. A 3D printable biodegradable polymer composite comprising:
 poly(glycerol sebacate acrylate) 30~50 wt %;
 a photo-initiator;
 polycaprolactone-diacrylate 30~40 wt %; and
 polyethyleneglycol-diacrylate 20~30 wt %;
 wherein a degree of acrylation of the poly(glycerol sebacate acrylate) is at a range of 5%~60%.

2. The 3D printable biodegradable polymer composite as claimed in claim 1, wherein:
 the photo-initiator is at a range of 0.05~5 wt %;
 the photo-initiator is a UV light initiator or a visible light initiator;
 the UV light initiator is TPO or prefluorinated dipheny titanocene; and
 the visible light initiator is TPO, prefluorinated dipheny titanocene or camphorquinone.

* * * * *